United States Patent
Leschinsky et al.

(10) Patent No.: US 9,585,618 B2
(45) Date of Patent: Mar. 7, 2017

(54) NERVE LOCATION DETECTION (71) Applicant: Empire Technology Development LLC, Wilmington, DE (US)

(72) Inventors: Boris Leschinsky, Mahwah, NJ (US); Jonathan R. Williams, Montville, NJ (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 436 days.

(21) Appl. No.: 14/237,084

(22) PCT Filed: Sep. 16, 2013

(86) PCT No.: PCT/US2013/060012
§ 371 (c)(1),
(2) Date: Feb. 4, 2014

(87) PCT Pub. No.: WO2015/038167
PCT Pub. Date: Mar. 19, 2015

(65) Prior Publication Data
US 2015/0223720 A1 Aug. 13, 2015

(51) Int. Cl.
*A61B 5/0492* (2006.01)
*A61B 5/00* (2006.01)
(Continued)

(52) U.S. Cl.
CPC .......... *A61B 5/4893* (2013.01); *A61B 5/0492* (2013.01); *A61B 5/04886* (2013.01);
(Continued)

(58) Field of Classification Search
CPC . A61B 5/4887; A61B 5/4893; A61B 5/04001; A61B 5/4041; A61B 5/4047; A61B 5/4052; A61B 90/11; A61B 90/13
See application file for complete search history.

(56) References Cited

U.S. PATENT DOCUMENTS 2,704,064 A 3/1955 Fizzell et al.
5,161,533 A 11/1992 Prass et al.
(Continued)

FOREIGN PATENT DOCUMENTS

EP 0637934 B1 7/2000

OTHER PUBLICATIONS

Byrne, K, and Tsui, B.C.H., "Practical Concepts in Nerve Stimulation: Impedance and Other Recent Advances," International Anesthesiology Clinics, vol. 49, Issue 4, pp. 81-90, Nov. 2011.
(Continued)

*Primary Examiner* — Adam J Eiseman
(74) *Attorney, Agent, or Firm* — Turk IP Law, LLC (57) ABSTRACT

Technologies are generally provided for identifying and marking the location of the laryngeal nerve prior to tissue dissection. A frame may include two multi-electrode stimulating probes, a slider with a guide movable between the two probes, and a marker probe including an anchor. The two probes supported on the frame may be inserted into tissue in a vicinity of the nerve, and a controller may sequentially stimulate the electrodes on each probe and measure electromyography (EMG) responses from each stimulated electrode. The controller may determine the nerve's location relative to the probes based on the measured EMG responses, where the location may include a lateral position between the probes and an estimated depth. The slider may be moved to the lateral position and the marker probe may be inserted through the slider to the determined depth. The anchor may be deployed next to the nerve to indicate the nerve location.

20 Claims, 6 Drawing Sheets (51) Int. Cl.
  *A61N 1/05* (2006.01)
  *A61N 1/08* (2006.01)
  *A61N 1/36* (2006.01)
  *A61B 5/0488* (2006.01)

(52) U.S. Cl.
  CPC ............ *A61B 5/6848* (2013.01); *A61B 5/706* (2013.01); *A61N 1/0502* (2013.01); *A61N 1/0551* (2013.01); *A61N 1/08* (2013.01); *A61N 1/36017* (2013.01); *A61B 2562/043* (2013.01); *A61N 1/36057* (2013.01)

(56) References Cited

U.S. PATENT DOCUMENTS

| | | | |
|---|---|---|---|
| 5,775,331 | A | 7/1998 | Raymond et al. |
| 6,533,732 | B1 | 3/2003 | Urmey |
| 7,010,352 | B2 | 3/2006 | Hogan |
| 7,918,802 | B2 | 4/2011 | Urmey |
| 8,083,685 | B2 * | 12/2011 | Fagin ............... A61B 5/04001 600/554 |
| 8,343,079 | B2 * | 1/2013 | Bartol ............... A61B 5/0488 600/301 |
| 8,979,767 | B2 * | 3/2015 | Bartol ............... A61B 5/0488 600/546 |
| 9,113,912 | B1 * | 8/2015 | Mehta ............... A61B 18/1492 |
| 9,119,628 | B1 * | 9/2015 | Mehta ............... A61B 18/1233 |
| 9,168,091 | B2 * | 10/2015 | Janssen ............. A61B 18/1477 |
| 9,283,031 | B2 * | 3/2016 | Janssen ............. A61B 18/1477 |
| 2002/0065481 | A1 * | 5/2002 | Cory ................ A61N 1/36021 604/21 |
| 2002/0161415 | A1 | 10/2002 | Cohen et al. |
| 2005/0182454 | A1 * | 8/2005 | Gharib ............... A61B 5/0488 607/48 |
| 2005/0283148 | A1 | 12/2005 | Janssen et al. |
| 2008/0269777 | A1 * | 10/2008 | Appenrodt ........... A61B 19/201 606/130 |
| 2010/0179410 | A1 | 7/2010 | Prass |
| 2012/0109004 | A1 | 5/2012 | Cadwell |
| 2012/0123292 | A1 | 5/2012 | Fagin et al. |

OTHER PUBLICATIONS

Randolph, G.W., et al., "Electrophysiologic Recurrent Laryngeal Nerve Monitoring During Thyroid and Parathyroid Surgery: International Standards Guideline Statement," Laryngoscope, vol. 121, pp. S1-S16, The American Laryngological Rhinological and Otological Society, Inc., Jan. 2011.

Tschopp, K., and Probst, R., "New aspects in surgery of the thyroid gland with intraoperative monitoring of the recurrent laryngeal nerve," vol. 73, No. 11, pp. 568-572, Nov. 1994.

Tsui, B.C.H., "Electrical Nerve Stimulation," in Atlas of Ultrasound and Nerve Stimulation, Chapter 2, pp. 9-18, Chan, V., et al., eds., Springer, Nov. 2007.

International Search Report and Written Opinion for PCT/US2013/060012 filed on Sep. 16, 2013, mailed on Dec. 19, 2013.

* cited by examiner

NERVE LOCATION DETECTION

CROSS-REFERENCE TO RELATED APPLICATION

This application is a U.S. Nationa Stage filing under 35 U.S.C. § 371 of PCT Application Ser. No. PCT/US13/060012 filed on Sep. 16, 2013. The PCT application is hereby incorporated by reference in its entirety.

Background

Unless otherwise indicated herein, the materials described in this section are not prior art to the claims in this application and are not admitted to be prior art by inclusion in this section.

Thyroid and parathyroid neck surgery involves a risk of severing a recurrent laryngeal nerve during dissection. Intraoperative nerve monitoring during thyroid and parathyroid surgery has gained widespread acceptance as an addition to nerve location by visual inspection. Intraoperatively, laryngeal nerve monitoring includes electromyography (EMG) observation, where changes in EMG activity are reported to the surgical team during such surgical events, such as retraction and dissection. The addition of EMG recordings to intraoperative nerve monitoring has been shown to prevent severing of recurrent laryngeal nerves during dissection.

Though the EMG monitoring system is widely used today, initial identification of the nerve location is difficult, time consuming, and uncertain. The manual procedure of EMG monitoring is often prone to artifacts, as well. As a result, primary nerve identification is done visually, while EMG monitoring is used typically for confirmation purposes.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

According to some examples, the present disclosure describes an electrode probe device for intraoperative nerve location identification. The electrode probe device may include a frame supporting at least a first probe and a second probe, where the first probe and the second probe each include two or more electrodes, a slider attached to the frame, the slider configured to be movable between the first and second probes, and a controller electrically coupled to the first and second probes, the controller configured to stimulate the electrodes.

According to other examples, the present disclosure also describes a method of identifying a location of a nerve employing an electrode probe device. The method may include inserting a first probe and a second probe in tissue in a vicinity of a nerve, where the first and second probes each include two or more electrodes, the first and second probes supported at a proximal end by a frame, stimulating the electrodes on the first and second probes employing a controller electrically coupled to the electrodes on the first and second probes, and recording an electromyography (EMG) response after stimulation of each individual electrode on the first and second probes.

According to further examples, the present disclosure also describes a system for identifying a location of a nerve employing an electrode probe device. The system may include a frame supporting at least a first probe and a second probe, where the first probe and the second probe each include two or more electrodes, a slider attached to the frame, the slider configured to be movable between the first and second probes, and a controller electrically coupled to the first and second probes, the controller configured to stimulate the electrodes.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, and/or devices related to providing an electrode probe device and system for intraoperative nerve location identification.

Briefly stated, technologies are generally provided for identifying and marking the location of the laryngeal nerve. A frame may include two multi-electrode stimulating probes, a slider with a guide movable between the two probes, and a marker probe including an anchor. The two probes supported on the frame may be inserted into tissue in a vicinity of the nerve, and a controller may sequentially stimulate the electrodes on each probe and measure electromyography (EMG) responses from each stimulated electrode. The controller may determine the nerve's location relative to the probes based on the measured EMG responses, where the location may include a lateral position between the probes and an estimated depth. The slider may be moved to the lateral position and the marker probe may be inserted through the slider to the determined depth. The anchor may be deployed next to the nerve to indicate the nerve location.

Figure 1A:
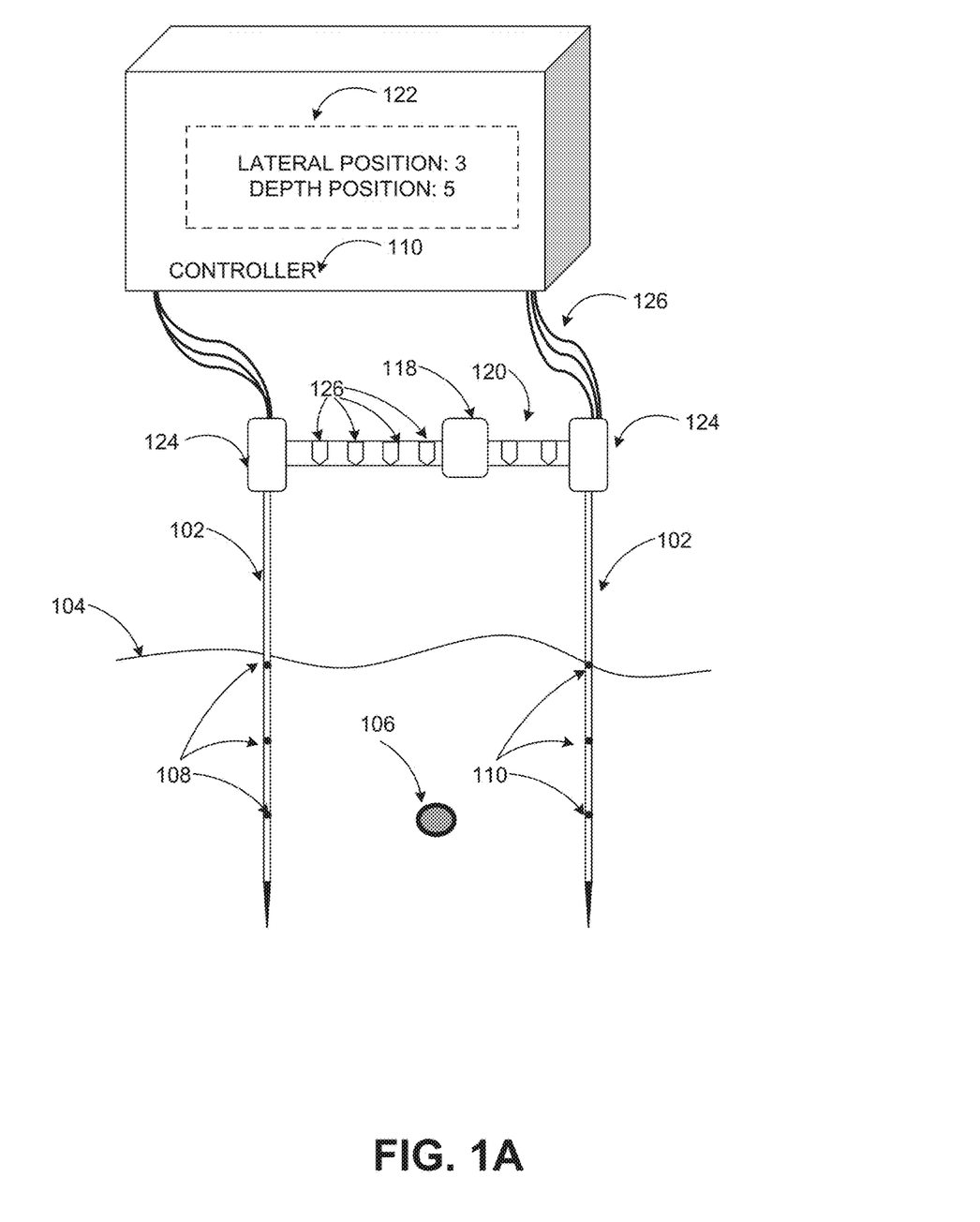
FIGS. 1A and 1B illustrate an example electrode probe device and marker probe.
Figure 1B:
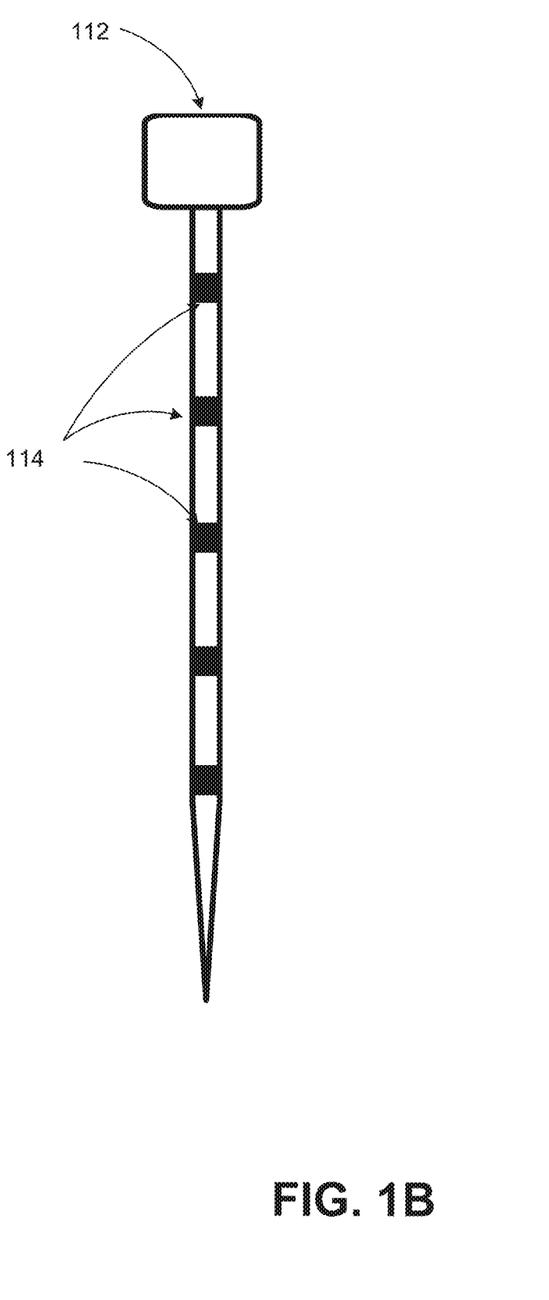

FIGS. 1A and 1B illustrate an example electrode probe device and marker probe, arranged in accordance with at least some embodiments as described herein. As illustrated in FIG. 1A, an electrode probe device system 100A may facilitate intraoperative nerve location. The electrode probe device system may include at least two parallel multi-electrode probes 102 supported on a frame 120, a plurality of lateral position markers 126 on the frame 120, a slider 118, a plurality of electrodes 108 disposed on the multi-electrode probes 102, a controller 110, and an electrode lead 126 electrically connecting the electrodes to the controller 110.

In an example embodiment, the two parallel multi-electrode probes 102, or needles, may be connected to the frame 120 at their respective hubs 124. The multi-electrode probes may be positioned substantially perpendicular with respect to the frame 120 and parallel with respect to each other. Each multi-electrode probe 102 may include a plurality of independent electrodes 108, and each electrode 108 may be electrically connected by the electrode lead 126 to the controller 110. The slider 118 may be configured to be laterally movable along the frame 120 between the hubs 124 of the multi-electrode probes 102. In some examples, the frame 120 may be a rod, and in other examples, the frame 120 may be configured in a circle or polygonal shape. In further embodiments, the frame 120 configured in the polygonal shape may support additional multi-electrode probes in order to provide additional electrodes to stimulate an EMG response from the nerve. Additional multi-electrode probes may enable increased accuracy in determining a location of the nerve based on detected EMG responses from the nerve.

In some embodiments, the lateral distance between the hubs 124 of the multi-electrode probes 102 on the frame 120 may be in a range from about 1 to about 2 inches, and the plurality of lateral position markers 126 on the frame 120 may be placed every about every ¼ of an inch to indicate a relative lateral position between the probes 102. The slider 118 may also incorporate a guide, which may be a hole or channel through which a marker probe, or anchor needle, may be inserted.

In an example scenario, a nerve may generate an electrical or EMG response in response to electrical stimulation by an electrode. A threshold level of electrical current stimulation may be required to generate a nerve response, and, in situ, the electrical stimulation may be impeded by bodily tissue surrounding the nerve. The more tissue impedance, the greater level of electrical stimulation by the electrodes may be required to generate an EMG response from the nerve. A known relationship of a distance of the stimulating electrode from the nerve 106 and a minimal stimulation current required for nerve activation and response may be used to estimate the location of the nerve relative to the stimulating electrodes disposed on the multi-electrode probes 102.

In a system according to embodiments, the multi-electrode probes 102 may be inserted through the skin 104 into neck tissue in an expected vicinity of the nerve 106 such that each probe may be positioned substantially on either side of the nerve 106. After insertion of the multi-electrode probes 102, the controller 110 may stimulate the electrodes 108 of each multi-electrode probe 102 to produce an EMG response from the nerve 106. The electrodes 108 on each of the multi-electrode probes 102 may be stimulated sequentially and individually, and an EMG response from the nerve 106 may be recorded after stimulation of each individual electrode. The EMG response may be recorded employing a sensing electrode, which may be an endotracheal tube with sensing electrodes configured to detect and record an EMG response. Based on the known distance-current relationship and the plurality of measured EMG responses recorded by the controller 110 after sequential and individual stimulation of each electrode on the multi-electrode probes 102, a distance between the probes and the nerve may be estimated. The known location, including depth and lateral position, of each electrode on the multi-electrode probes 102 may facilitate triangulating the location of the nerve 106 relative to the multi-electrode probes 102.

In an example embodiment, the controller 110 may determine the location of the nerve 106 as a two-dimensional location 122 relative to the two multi-electrode probes 102, where the two dimensional location 122 may include a lateral distance between the multi-electrode probes 102 and a depth. An EMG response may not be recorded if the stimulation level does not meet the threshold level for stimulating the nerve 106. The process of stimulating the electrodes 108 individually and sequentially may be conducted once or several times with gradually increasing levels of electrical current in order to generate EMG responses from the nerve 106. In a system according to embodiments, once the location of the nerve 106 relative to the probes 102 is determined, a marker probe may be employed to deploy and position an anchor next to the nerve 106 to indicate the location of the nerve 106.

FIG. 1B illustrates an example marker probe, arranged in accordance with at least some embodiments as described herein. An example marker probe 112 may house a deployable anchor which may be deployed in position next to the nerve 106 to indicate the nerve's location. The marker probe 112 may include a plurality of depth markers 114, to indicate a depth of the marker probe 112 as it is inserted into the neck tissue. In some examples, the depth markers 114 may be placed about every ¼ of an inch, though any desirable depth interval may be employed.

Figure 2:
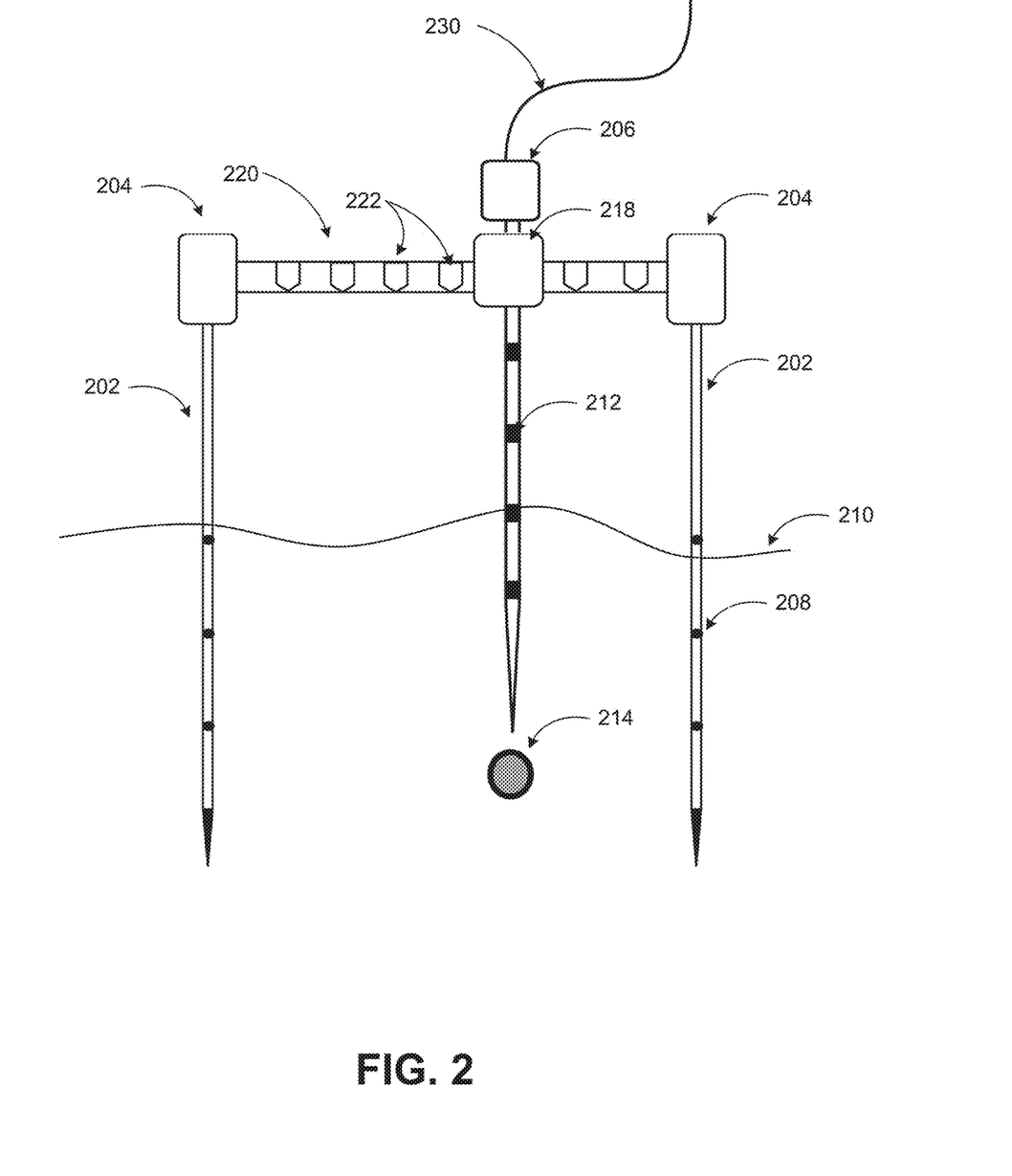
FIG. 2 illustrates an example electrode probe device with a marker probe placed near a nerve.

FIG. 2 illustrates an example electrode probe device with a marker probe placed near a nerve, arranged in accordance with at least some embodiments as described herein. As described above in conjunction with FIG. 1A, an electrode probe device system for intraoperative nerve location identification may include at least two parallel multi-electrode probes 202 supported on a frame 220 at fixed hubs 204, a plurality of position markers 222 on the frame 220, a plurality of electrodes 208 disposed on the probes 202, and a slider 218. The electrode probe device system may also include a marker probe 206 for deploying an anchor to indicate a location of a nerve 214.

In a system according to embodiments, the multi-electrode probes 202 may be inserted through skin 210 in a vicinity of the nerve 214 such that each multi-electrode probe is positioned on either side of the nerve 214. After insertion, a controller may individually and sequentially energize each of the plurality of electrodes 208 disposed on the first and the second multi-electrode probes 202 in rapid succession. The controller may measure and record an EMG response detected from the nerve 214 in response to stimulation by the electrodes 208. Based on a known distance-current relationship and the plurality of measured EMG responses recorded by the controller after sequential and individual stimulation of the electrodes 208, a distance between the probes 202 and the nerve may be estimated.

The distance between the first and the second multi-electrode probes 202 and the nerve 214 may be identified in a two dimensional plane defined by the first and the second multi-electrode probes 202 and represented as a lateral position and depth position relative to the multi-electrode probes 202 on the frame 220. To guide the marker probe 206 to the determined nerve location, the slider 218 may be moved to the determined lateral position as indicated by the position markers 222 on the frame 220. The slider 218 may include a channel or guide for enabling insertion of the marker probe 206 through the slider 218. The marker probe 206 may be inserted through the slider 218 to the determined depth. The marker probe 206 may include a plurality of depth markers 212 to indicate the depth of insertion as the marker probe 206 is inserted through the skin 210. After insertion of the marker probe 206 to the determined depth of the nerve 214, an anchor 230 may be deployed and left behind next to the nerve 214 to guide confident and fast dissection of tissues near the nerve 214 without the danger of inadvertent nerve severing.

In an example embodiment, the marker probe 206 may also include one or more stimulating electrodes at its distal end such that the proximity of the marker probe 206 to the nerve 214 may be confirmed prior to anchor 230 deployment by stimulating the electrodes on the marker probe 206 and measuring an EMG response from the nerve 214.

Figure 3:
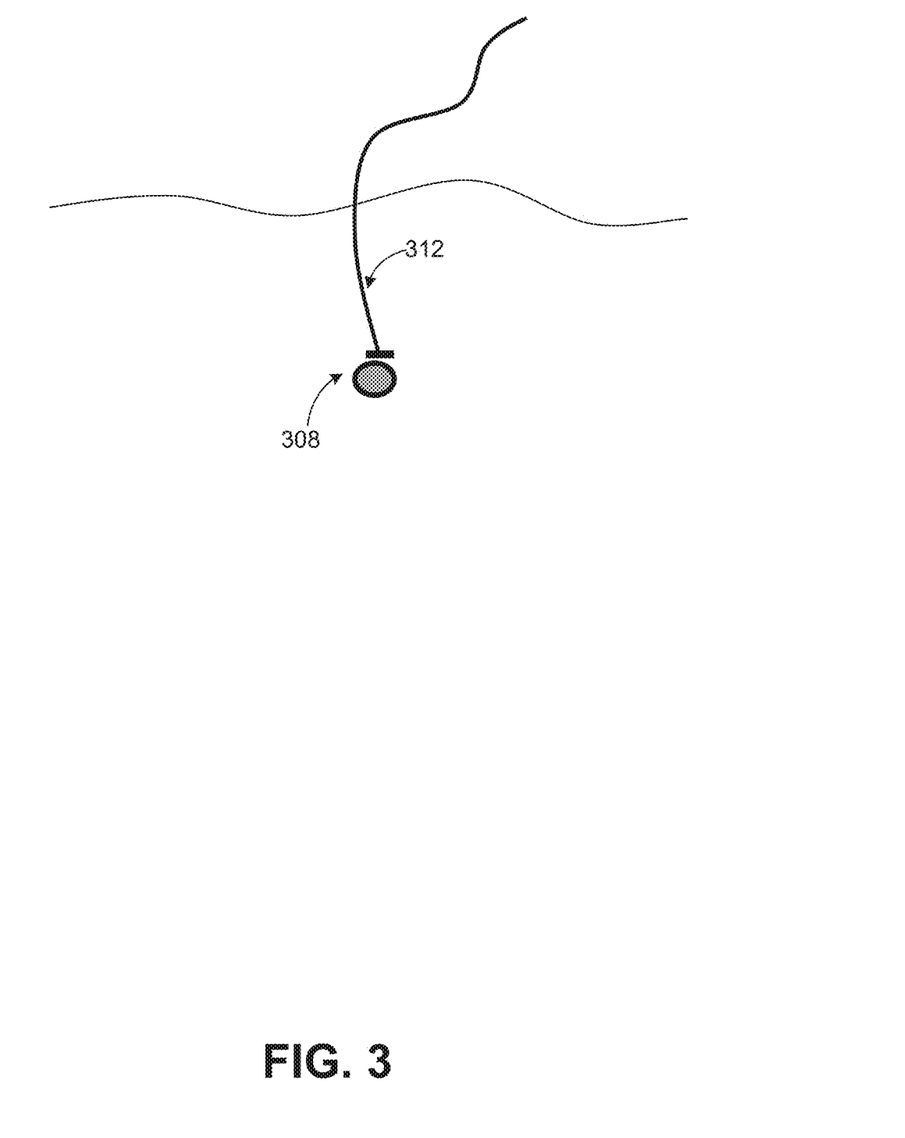
FIG. 3 illustrates an example anchor placed near a nerve.

FIG. 3 illustrates an example anchor deployed near the location of a nerve. After insertion of a marker probe near a location of a nerve 308, an anchor 312 may be deployed next to the nerve 308 to indicate the location of the nerve 308. An example anchor may include a dye or a barb. Other anchors may be a hook, a T-shaped ends, or a spider barb for example. The anchor 312 may be left next to the nerve 308 to guide confident and fast dissection of tissues without the danger of inadvertent nerve severing. After the anchor 312 is deployed near the nerve 308, the electrode probe device system including the multi-electrode probes supported on a frame and the marker probe may be removed.

Figure 4:
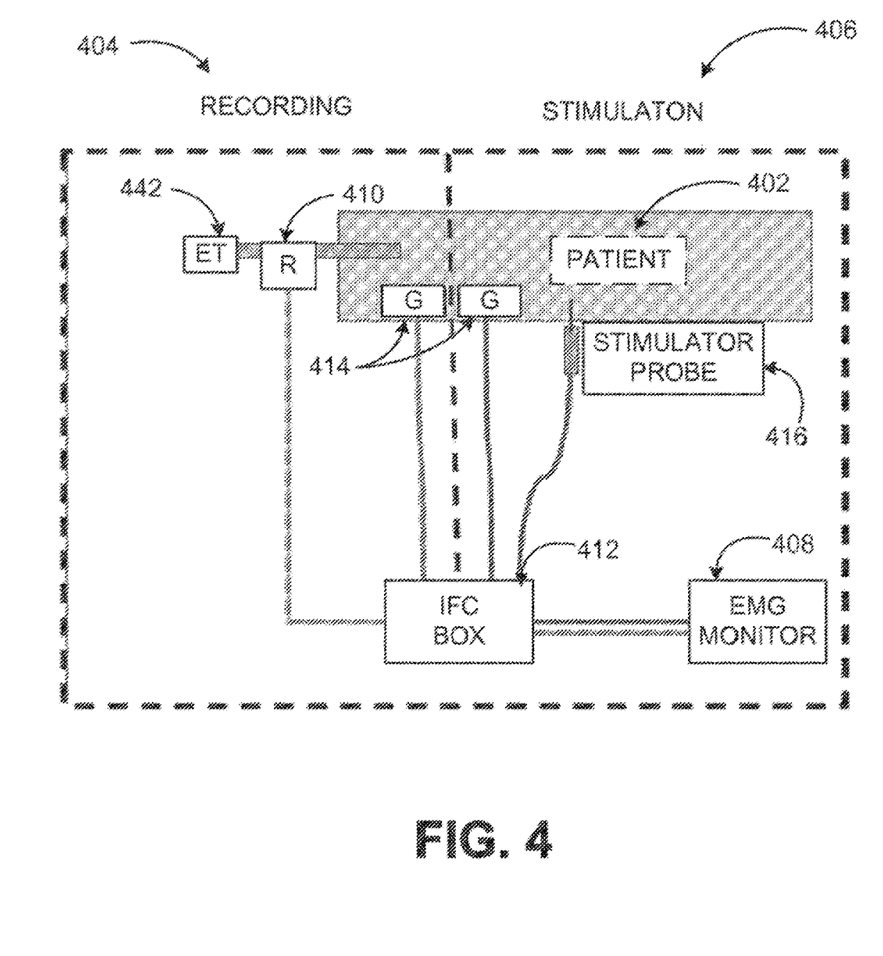
FIG. 4 illustrates an example schematic of an electrode monitoring set-up during surgery.

FIG. 4 illustrates an example schematic of an Electromyography (EMG) monitoring set-up during surgery, where a nerve detection system may include a recording side 404 and a stimulation side 406, connected by an interface connector box (IFC Box) 412. The recording side 404 may include a sensing electrode such as an endotracheal tube (ET) 442, recording electrodes (R) 410, and ground electrodes (G) 414. The stimulation side 406 may include a patient 402, a stimulator probe 416, an electromyography (EMG) monitor 408, and additional ground electrodes (G) 414. The stimulator probe 416 may include two multi-electrode anchor needles.

The recording side 404 may include a ground electrode 414 and an endotracheal tube 442, which may be equipped with recording electrodes 410 located at an expected position of the vocal cords. The stimulation side 406 may include aground electrode 414 and a stimulator probe(s) 416 which may be equipped with a plurality of stimulating electrodes. The stimulating electrodes, as previously described may be included on two or more probes supported by a frame and configured to be inserted near a location of a laryngeal nerve. The electrodes may be connected to an interface connector box 412, which in turn may be attached to an EMG monitor 408. The EMG monitor 408 may have a stimulation channel, configured to supply current to the stimulator probes 416, and a recording channel configured to measure an EMG response of the nerve detected by the recording electrodes 410. Electrical stimulation signal may be supplied continuously to the stimulating electrode. When the nerve is activated by the stimulator probe 416, the signal may trigger stimulation of the nerve causing it to generate a certain EMG response.

The EMG monitor 408 may produce an electromyogram, detecting the electrical potential generated by muscle cells when the cells are electrically activated. The signals may then be analyzed to detect activation level, and to facilitate deter a location of the nerve relative to the stimulator probes 416 based on a known distance-stimulation relationship of the nerve.

Figure 5:
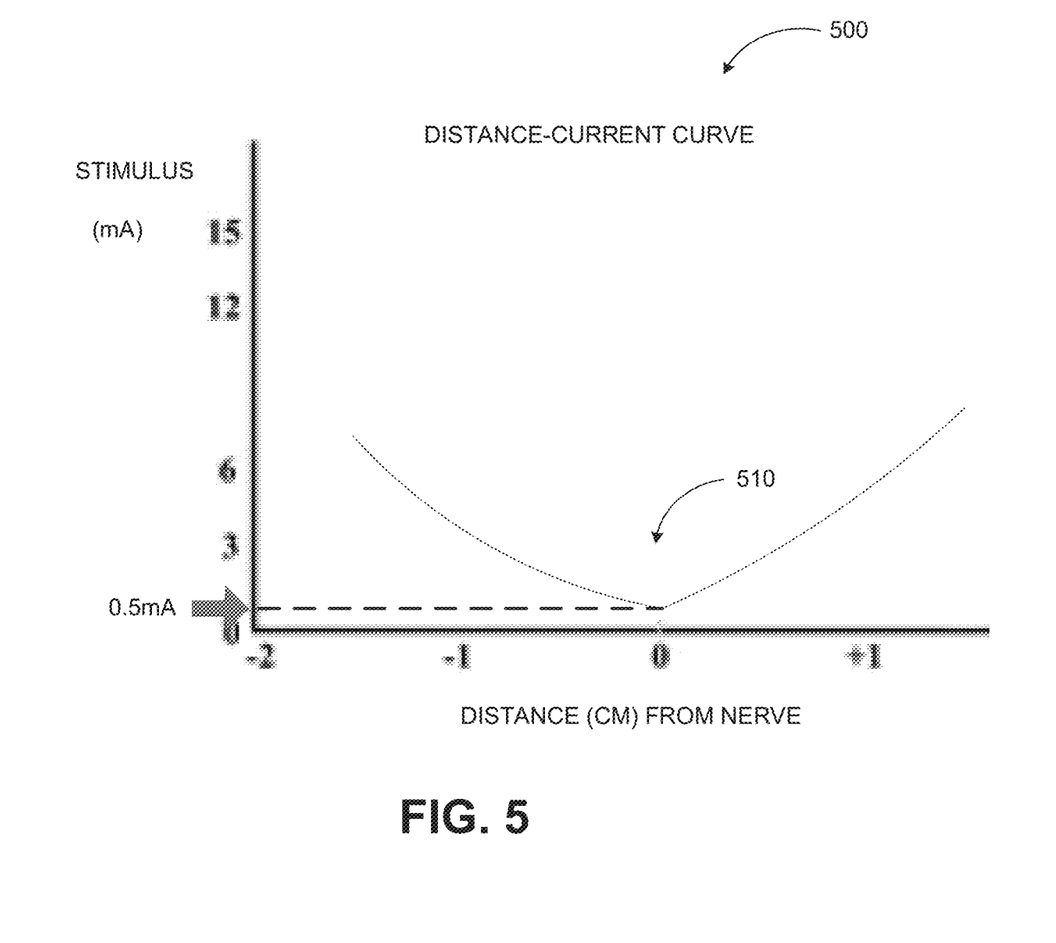
FIG. 5 illustrates an example distance current curve for a probe in tissue, all arranged in accordance with at least some embodiments as described herein.

FIG. 5 illustrates an example distance-current curve for a probe in tissue. Graph 500 illustrates a distance-current curve for a level of stimulation required to generate an EMG response when the stimulating electrode is at various distances from the nerve. Generally, as the distance increases between the nerve and the stimulating electrode, a higher stimulus current is required to generate an EMG response from the nerve. The current varies with the inverse of the square of the distance according to Coulomb's law, where $I=k(i/r^2)$ and I=current required, k=constant, i=minimum current and r=distance from the nerve. When the probe is somewhat away from the nerve, an electrical signal may have to travel through tissue and may encounter certain electrical resistance. Below a threshold stimulating current level (510), the nerve may not be stimulated, and an EMG response may not be recorded. Above the threshold stimulating current level, the greater the distance from the nerve, the greater the tissue impedance, causing the signal to lose some of its strength. As a result, the level of electrical current needed to generate an EMG response from the nerve may be proportional to the distance between the immersed electrode and the nerve.

While embodiments have been discussed above using specific examples, components, and configurations, they are intended to provide a general guideline to be used for providing a device to detect a location of a nerve. These examples do not constitute a limitation on the embodiments, which may be implemented using other components, modules, and configurations using the principles described herein. Furthermore, actions discussed above may be performed in various orders, especially in an interlaced fashion.

According to some examples, the present disclosure describes an electrode probe device for intraoperative nerve location identification. The electrode probe device may include a frame supporting at least a first probe and a second probe, where the first probe and the second probe each include two or more electrodes, a slider attached to the frame, the slider configured to be movable between the first and second probes, and a controller electrically coupled to the first and second probes, the controller configured to stimulate the electrodes.

According to some examples, the electrode probe device may also include a third probe configured to be inserted at a position between the first and second probes. The third probe may include at least one electrode. The first, second, and third probes may be positioned substantially perpendicular with respect to the frame and parallel with respect to each other.

According to some examples, the slider may include a hole for enabling insertion of the third probe. The third probe may include a plurality of depth marks corresponding to predefined distances. An anchor may be configured to be inserted through the third probe to mark the location of the nerve. The anchor may be selected from one or more of: a dye, a barb. The anchor may be configured to remain at the location of the nerve when the probes may be removed.

According to some examples, the frame may include a plurality of marks corresponding to predefined lateral distances between the first and second probes. The controller may be configured to stimulate each electrode on the first probe and the second probe individually. The controller may be configured to stimulate each electrode on the first probe and the second probe sequentially.

According to some examples, an electromyography (EMG) response may be recorded after stimulation of each individual electrode on the first and second probes. The controller may be configured to vary an electrical current for stimulating the electrodes. The controller may be configured to estimate an approximate location of a nerve by determining a distance of each of the first and second probes from the nerve based on the recorded EMG response of each stimulated electrode. The frame may be configured to support additional probes. The frame may be configured in a substantially polygonal shape.

According to other examples, the present disclosure also describes a method of identifying a location of a nerve employing an electrode probe device. The method may include inserting a first probe and a second probe in tissue in a vicinity of a nerve, where the first and second probes each include two or more electrodes, the first and second probes supported at a proximal end by a frame, stimulating the electrodes on the first and second probes employing a controller electrically coupled to the electrodes on the first and second probes, and recording an electromyography (EMG) response after stimulation of each individual electrode on the first and second probes.

According to some examples, the method may also include stimulating each electrode on the first and second probes individually and sequentially. The method may also include stimulating each electrode at varying levels of electrical current supplied by the controller. The method may also include estimating an approximate distance of each of the first probe and the second probe from a nerve based on the recorded EMG response of each stimulated electrode.

According to other examples, the method may also include estimating a location of the nerve by triangulating the location based on a location of the first and second probes and the approximated distance of each of the first probe and the second probe from the nerve. The method may also include moving a slider to a position on the frame between the first and second probes corresponding to an estimated lateral location of the nerve. The frame may include a plurality of marks corresponding to a predefined lateral distance between the first and second probes.

According to other examples, the method may also include inserting a third probe through the slider to a depth corresponding to an estimated vertical location of the nerve. The third probe may include a plurality of marks corresponding to a predefined vertical distance depth. The method may also include, after insertion of the third probe, stimulating at least one electrode included on the third probe to confirm a location of the nerve. The method may also include inserting an anchor through the third probe to mark the location of the nerve. The method may also include removing the frame including the first, second and third probes, and leaving the anchor in position in tissue near the nerve.

According to further examples, the present disclosure also describes a system for identifying a location of a nerve employing an electrode probe device. The system may include a frame supporting at least a first probe and a second probe, where the first probe and the second probe each include two or more electrodes, a slider attached to the frame, the slider configured to be movable between the first and second probes, and a controller electrically coupled to the first and second probes, the controller configured to stimulate the electrodes.

According to other examples, the system may also include a third probe configured to be inserted at a position between the first and second probes, where the third probe may include at least one electrode. The first, second, and third probes may be positioned substantially perpendicular with respect to the frame and parallel with respect to each other. The slider may include a hole for enabling insertion of the third probe.

According to other examples, the third probe may include a plurality of depth marks corresponding to predefined distances. The frame may include a plurality of marks corresponding to predefined lateral distances between the first and second probes. The controller may be configured to stimulate each electrode on the first probe and the second probe individually.

According to other examples, the controller may be configured to stimulate each electrode on the first probe and the second probe sequentially. An electromyography (EMG) response may be recorded after stimulation of each individual electrode on the first and second probes. The controller may be configured to vary an electrical current for stimulating the electrodes. The controller may be configured to estimate an approximate location of a nerve by determining a distance of each of the first and second probes from the nerve based on the recorded EMG response of each stimulated electrode.

According to other examples, an anchor may be configured to be inserted through a third probe to mark the location of the nerve. The anchor may be selected from one or more of: a dye, and a barb. The anchor may be configured to remain at the location of the nerve when the probes may be removed. The frame may be configured to support additional probes. The frame may be configured in a substantially polygonal shape.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected," or "operably coupled," to each other to achieve the desired functionality, and any two components capable of being so associated may also be viewed as being "operably couplable," to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and an forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An electrode probe device for intraoperative nerve location identification, the electrode probe device comprising:
    a frame supporting at least a first probe and a second probe, wherein each of the first probe and the second probe include two or more electrodes;
    a slider attached to the frame, the slider configured to be moved to a position on the frame between the first and second probes corresponding to an estimated lateral location of a nerve;
    a third probe configured to be inserted at a position between the first and second probes, wherein the third probe includes at least one electrode; and
    a controller electrically coupled to the first, second and third probes, the controller configured to stimulate the two or more electrodes of each of the first probe and the second probe to identify a location of the nerve, and stimulate the at least one electrode of the third probe to confirm the location of the nerve.

2. The electrode probe device of claim 1, wherein the third probe includes a plurality of depth marks corresponding to predefined distances.

3. The electrode probe device of claim 2, wherein an anchor is configured to be inserted through the third probe to mark the location of the nerve.

4. The electrode probe device of claim 1, wherein the frame includes a plurality of marks corresponding to predefined lateral distances between the first and second probes.

5. The electrode probe device of claim 1, wherein the frame is configured in a substantially polygonal shape.

6. The electrode probe device of claim 1, wherein the controller is configured to vary an electrical current for stimulating the two or more electrodes of each of the first probe and the second probe.

7. The electrode probe device of claim 1, wherein the controller is configured to stimulate each electrode on the first probe and the second probe individually or sequentially.

8. The electrode probe device of claim 7, wherein an electromyography (EMG) response is recorded after stimulation of each of the two or more electrodes of each of the first probe and the second probe.

9. The electrode probe device of claim 8, wherein the controller is configured to estimate an approximate location of a nerve by determining a distance of each of the first and second probes from the nerve based on the EMG response.

10. The electrode probe device of claim 1, wherein the frame is configured to support additional probes.

11. The electrode probe device of claim 1, wherein the slider includes a hole for enabling insertion of the third probe.

12. A system for identifying a location of a nerve employing an electrode probe device, the system comprising:
- a frame supporting at least a first probe and a second probe, wherein each of the first probe and the second probe include two or more electrodes;
- a slider attached to the frame, the slider configured to be moved to a position on the frame between the first and second probes corresponding to an estimated lateral location of a nerve;
- a third probe configured to be inserted at a position between the first and second probes, wherein the third probe includes at least one electrode; and
- a controller electrically coupled to the first, second and third probes, the controller configured to stimulate the two or more electrodes of each of the first probe and the second probe to identify a location of the nerve, and stimulate the at least one electrode of the third probe to confirm the location of the nerve.

13. The system of claim 12, wherein the first, second, and third probes are positioned substantially perpendicular with respect to the frame and parallel with respect to each other.

14. The system of claim 12, wherein the slider includes a hole for enabling insertion of the third probe.

15. The system of claim 12, wherein the controller is configured to stimulate each electrode on the first probe and the second probe individually.

16. The system of claim 12, wherein the controller is configured to estimate an approximate location of a nerve by determining a distance of each of the first and second probes from the nerve based on an electromyography (EMG) response recorded after stimulation of each individual electrode on the first and second probes.

17. The system of claim 12, wherein an anchor is configured to be inserted through the third probe to mark the location of the nerve.

18. The system of claim 17, wherein the anchor is configured to remain at the location of the nerve when the first probe and the second probe are removed.

19. The system of claim 12, wherein the third probe is inserted through the slider to a depth corresponding to an estimated vertical location of the nerve.

20. The system of claim 12, wherein the third probe includes a plurality of marks corresponding to a predefined vertical distance depth.

* * * * *

UNITED STATES PATENT AND TRADEMARK OFFICE
CERTIFICATE OF CORRECTION

PATENT NO. : 9,585,618 B2
APPLICATION NO. : 14/237084
DATED : March 7, 2017
INVENTOR(S) : Leschinsky et al.

It is certified that error appears in the above-identified patent and that said Letters Patent is hereby corrected as shown below:

In the Specification

In Column 2, Lines 28-29, delete "all arranged....herein." and insert the same at Line 29, as a new sub point.

In Column 5, Line 50, delete "aground" and insert -- a ground --, therefor.

In Column 6, Line 3, delete "deter a" and insert -- determining a --, therefor.

In Column 9, Lines 63-64, delete "and possible" and insert -- and all possible --, therefor.

In Column 10, Lines 11-12, delete "an forth." and insert -- so forth. --, therefor.

Signed and Sealed this
Twenty-third Day of May, 2017

Michelle K. Lee
*Director of the United States Patent and Trademark Office*